US007851162B2

(12) United States Patent
Lubiñski et al.

(10) Patent No.: US 7,851,162 B2
(45) Date of Patent: Dec. 14, 2010

(54) DETERMINING A PREDISPOSITION TO CANCER

(76) Inventors: Jan Lubiñski, Ul. Akacjowa 2, Szczecin (PL) 71-253; Janina Suchy, ul. Ledochoskiego 7/10, Szczecin (PL) 71-004; Grzegorz Kurzawski, ul. Tomaszowska 24/9, Szczecin (PL) 71-671; Tadeusz Dêbniak, ul. Rteciowa 13, Szczecin (PL) 70-736; Cezary Cybulski, 72-005 Przeclaw 58c/8, Przeclaw (PL) 72-005

(*) Notice: Subject to any disclaimer, the term of this patent is extended or adjusted under 35 U.S.C. 154(b) by 114 days.

(21) Appl. No.: 12/220,761

(22) Filed: Jul. 28, 2008

(65) Prior Publication Data

US 2009/0092984 A1  Apr. 9, 2009

Related U.S. Application Data

(62) Division of application No. 11/037,657, filed on Jan. 18, 2005, now Pat. No. 7,407,755.

(60) Provisional application No. 60/565,724, filed on Apr. 27, 2004, provisional application No. 60/563,089, filed on Apr. 16, 2004, provisional application No. 60/536,746, filed on Jan. 15, 2004.

(51) Int. Cl.
*C12Q 1/68* (2006.01)
*C12P 19/34* (2006.01)
*C07H 21/04* (2006.01)

(52) U.S. Cl. ............... 435/6; 435/91.2; 536/23.5; 536/24.3

(58) Field of Classification Search .................. None
See application file for complete search history.

(56) References Cited

U.S. PATENT DOCUMENTS

| 2002/0004206 A1 | 1/2002 | Berger et al. | |
|---|---|---|---|
| 2003/0138928 A1 | 7/2003 | Carson et al. | |
| 2003/0175721 A1* | 9/2003 | Box et al. | 435/6 |

FOREIGN PATENT DOCUMENTS

| WO | WO 99/29903 A | 6/1999 |
|---|---|---|
| WO | WO 2005/068659 | 7/2005 |

OTHER PUBLICATIONS

Lakatos, Peter Laszlo et al. Common NOD2/CARD15 variants are not assoicated with susceptibility or the clinicopathologic characteristics of sporadic colorectal cancer in Hungarian patients. 2007. BMC Cancer. vol. 7 No. 54 pp. 1-5.*
Magnowski P et al. The 3020insC NOD2 gene mutation in patients with ovarian cancer. 2008 Ginekol Pol vol. 79 No. 8 pp. 544-549.*
Berns, Emjj et al. Infrequent CDKN2 (MTS1/p16) gene alterations in human primary breast cancer. 1995. British Journal of Cancer vol. 72 pp. 964-967.*

The Gene Card for NOD2 found online at http://www.genecards.org/cgi-bin/carddisp.pl?gene=NOD2&search=nod2 and accessed Feb. 12, 2010.*
The Gene Card for CDKN2A found online at http://www.genecards.org/cgi-bin/carddisp.pl?gene=CDKN2A&search=cdkn2a and accessed Feb. 12, 2010.*
International Search Report issued by the International Searching Authority (ISA/EP) on Jul. 28, 2005 in connection with PCT International Application No. PCT/PL2005/000006, filed Jan. 15, 2005.
International Preliminary Report on Patentability issued Jul. 17, 2006 in connection with PCT International Application No. PCT/PL2005/000006, filed Jan. 15, 2005.
Written opinion of the International Searching Authority issued on Jul. 15, 2006 in connection with PCT International Application No. PCT/PL2005/000006.
Examination Report issued Nov. 5, 2009 in connection with European Patent Application No. 05704666.6.
May 14, 2010 Reply to the Examination Report issued Nov. 5, 2009 in connection with European Patent Application No. 05704666.6.
Seppälä, E.H., et al. (2003) "CHEK2 variants associate with hereditary prostate cancer," *British Journal of Cancer* 89:1966-1970.
Meijers-Heijboer, Hanne, et al. (2002) "Low-penetrance susceptibility to breast cancer due to CHEK2(*)1100delC in noncarriers of BRCA1 or BRCA2 mutation," *Nature Genetics* 31:55-59.
Vahteristo, Pia, et al. (2002) "A CHEK2 genetic variant contributing to a substantial fraction of familial breast cancer," *American Journal of Human Genetics* 71:432-438.
Huzarski, Tomasz, et al. (2005) "Pathology of breast cancer in women with constitutional CHEK2 mutations," *Breast Cancer Research and Treatment* 90:187-189.
Cybulski, Cezary, et al. (2004) "A novel founder CHEK2 mutation is associated with increased prostate cancer risk," *Cancer Research* 64:2677-2679.
File History of U.S. Appl. No. 11/037,657, filed Jan. 18, 2005.
Bell et al., Heterozygous Germ Line hCHK2 Mutations in Li-Fraumeni Syndrome, (1999) Science, vol. 386, pp. 2528-2531.
Dong et al., "Mutations in CHEK2 Associated with Prostate Cancer Risk", (2003) American Journal of Human Genetics, vol. 72, pp. 270-280.
Dufault et al., "Limited International Relevance of the CHEK2 gene in hereditaty breast cancer", International Journal of Cancer, vol. 110, pp. 320-325, Pub online Feb. 27, 2004.
Ingvarsson et al., "Mutation analysis of the CHK2 gene in breast carcinoma and other cancers", (2002), Breast Cancer Research, vol. 4, pp. 1-6.
Verhagen, A., "Is the p value really so significant", (2004), Australian Journal of Physiotherapy, vol. 50, pp. 261-262.

* cited by examiner

*Primary Examiner*—Carla Myers
*Assistant Examiner*—Amanda Shaw
(74) *Attorney, Agent, or Firm*—Gary J. Gershik; Cooper & Dunham LLP

(57) ABSTRACT

The present invention relates to methods and kits for determining a predisposition and surveillance protocols for developing cancer of various sites due to specific mutation in at least one allele of CHEK2 gene and/or at least one allele of NOD2 gene and/or at least one allele of CDKN2A gene.

19 Claims, 3 Drawing Sheets

Fig. 1

```
   1 ctcctccgag cactcgctca cggcgtcccc ttgcctggaa agataccgcg gtccctccag
  61 aggatttgag ggacagggtc ggaggggggct cttccgccag caccggagga agaaagagga
 121 ggggctggct ggtcaccaga gggtggggcg gaccgcgtgc gctcggcggc tgcggagagg
 181 gggagagcag gcagcgggcg gcggggagca gcatggagcc ggcggcgggg agcagcatgg
 241 agccttcggc tgactggctg gccacggccg cggcccgggg tcgggtagag gaggtgcggg
 301 cgctgctgga ggcgggggcg ctgcccaacg caccgaatag ttacggtcgg aggccgatcc
 361 aggtcatgat gatgggcagc gcccgagtgg cggagctgct gctgctccac ggcgcggagc
 421 ccaactgcgc cgaccccgcc actctcaccc gacccgtgca cgacgctgcc cgggagggct
 481 tcctggacac gctggtggtg ctgcaccggg ccggggcgcg gctggacgtg cgcgatgcct
 541 ggggccgtct gcccgtggac ctggctgagg agctgggcca tcgcgatgtc gcacggtacc
 601 tgcgcgcggc tgcggggggc accagaggca gtaaccatgc ccgcatagat gccgcggaag
 661 gtccctcaga catccccgat tgaaagaacc agagaggctc tgagaaacct cgggaaactt
 721 agatcatcag tcaccgaagg tcctacaggg ccacaactgc ccccgccaca acccaccccg
 781 ctttcgtagt tttcatttag aaaatagagc ttttaaaaat gtcctgcctt ttaacgtaga
 841 tatatgcctt ccccactac cgtaaatgtc catttatatc atttttata tattcttata
 901 aaaatgtaaa aaagaaaaac accgcttctg ccttttcact gtgttggagt tttctggagt
 961 gagcactcac gccctaagcg cacattcatg tgggcatttc ttgcgagcct cgcagcctcc
1021 ggaagctgtc gacttcatga caagcatttt gtgaactagg gaagctcagg ggggttactg
1081 gcttctcttg agtcacactg ctagcaaatg gcagaaccaa agctcaaata aaaataaaat
1141 aattttcatt cattcactca aaa
```

Fig. 2

```
49,321,101  tgagcaggat gtgtctaagg gacaggtggg cttcagtaga ctggctaact
49,321,151  cctgcagtct ctttaactgg acagtttcaa gaggaaaacc aagaatcctt
49,321,201  gaagctcacc attgtatctt cttttccagg ttgtccaata actgcatcac
49,321,251  ctacctaggg gcagaagccc tcctgcaggcc ccttgaaagg aatgacacca
49,321,301  tcctggaagt ctggtaaggc ccctgggcag gcctgtttta gctctccgaa
```

Fig. 3 acagaatgtgtgaatgacaactactggtttgggagggacaaaagctgtgaatattgcttt
gatgaaccactgctgaaaagaacagataaataccgaacatacagcaagaaacactttcgg
attttcagggtaggtaatgaatacccatgtatctaggagagctggtaatttggtcattgt
ttttagatattttcccactataaatctctgctattcaaagtctgaaacaaaatgttctct
attttaggaagtgggtcctaaaaactcttacattgcatacatagaagatcacagtggcaa
tggaacctttgtaaatacagagcttgtagggaaaggaaaacgccgtcctttgaataacaa
ttctgaaattgcactgtcactaagcagaaataaaggtaatat

DETERMINING A PREDISPOSITION TO CANCER

CROSS-REFERENCE TO RELATED APPLICATIONS

This application is a divisional of U.S. Ser. No. 11/037,657, filed Jan. 18, 2005, now U.S. Pat. No. 7,407,755, issued Aug. 5, 2008, claiming benefit of U.S. Provisional Application No. 60/565,724, filed Apr. 27, 2004, U.S. Provisional Application No. 60/563,089, filed Apr. 16, 2004, and U.S. Provisional Patent Application Ser. No. 60/536,746, filed Jan. 15, 2004, the contents of all of which are hereby incorporated by reference into this application.

FIELD OF THE INVENTION

The present invention relates to methods and kits for determining a subject's predisposition for developing cancer of various sites, especially a predisposition of low penetrance.

BACKGROUND OF THE INVENTION

Up to now MSH2/MLH1 and APC gene mutations have been considered as the major cause of inherited colorectal cancer (CRC). Carriers of mutations within the above genes have a very high risk of cancer, but they constitute only a few percent only of all CRC.

It has been reported that having a chronic inflammatory status longer than 8-10 years is also related to an increased risk of CRC. Despite long-term efforts aimed to find the way of diagnosing the predisposition to CRC, a procedure allowing this has not yet been discovered.

NOD2 gene has been mapped on chromosome 16q12 (Ogura et al., J. Biol. Chem. 2001; 276: 4812-4818). It contains 12 exons and encodes a protein composed of 1040 of amino acids. In 2001, a correlation between 3020insC in exon 11 of NOD2 and the occurrence of Crohn's disease (CD) was shown. PCT Publication WO 02/44426 presents the sequence of NOD2 as well as the relation between distinct variants of this gene (including a variant with 3020insC) and CD. CD and ulcerative colitis are recognized as inflammatory bowel diseases.

CHEK2, (also known as CHK2 [MIM 604373]) is located on chromosome 22q and encodes die human analogue of yeast Cds1 and Rad53, which are checkpoint kinases. Activation of these proteins in response to DNA damage prevents cellular entry into mitosis. CHEK2 is activated through phosphorylation by ATM in response to DNA damage induced by ionizing radiation. Activated CHEK2 phosphorylates BRCA1 and TP53 proteins, regulating tumor suppressor function of these proteins (Matsuoka et al., Proc. Natl. Acad. Sci. USA, 97: 10389-10394, 2000. Chaturvedi et al. Oncogene, 18: 4047-54, 1999, Ahn et al. Cancer Res., 60: 5934-6, 2000, Falck et al. Nature, 410: 842-847, 2001, Chehab et al. Genes Dev., 14: 278-288, 2000, Shieh et al., Genes Dev., 14: 289-300, 2000, Lee et al. Nature, 404: 201-204, 2000.).

In Poland there are three polymorphic variants of CHEK2, which in aggregate are present in 5.7% of the population; two of these (1100delC and IVS2+ IG>A) are rare and result in premature protein truncation. The third is a common missense variant (I157T) that results in the substitution of an isoleucine for a threonine. All three variants have been found to be associated with a predisposition to prostate cancer. The CHEK2 protein is expressed in a wide range of tissues and the lull range of cancers associated with inactivating CHEK2 mutations has not yet been determined.

The IVS2+1G>A mutation creates a 4-bp insertion due to abnormal splicing, creates premature protein termination codon in exon 3 and leads to the disruption of protein expression. There are no reports suggesting correlation between the CHEK2 IVS2+1G>A allele alone and increased predisposition to cancer. The IVS2+1G>A variant has been reported previously only in a single family with prostate cancer in the United States (Dong et al., Am. J. Hum. Genet., 72: 270-280, 2003). However, the IVS2+1G>A allele did not segregate with prostate cancer within this family and it was not proven that the IVS2+1G>A confer increased prostate cancer risk.

The 1100delC variant of CHEK2 is present with a 1.1-1.4% frequency in normal population in the European countries studied so far but in North America the allele appears to be relatively rare (CHEK2 Breast Cancer Consortium, Nature Genet., 31: 55-59, 2002; Offit et al., BMC Med. Genet. 15: 1, 2003). This allele has been found to confer a modestly elevated risk of breast and prostate cancer.

The most common CHEK2 variant identified so far was Ile157Thr. The role of this variant, however, is controversial, even though both genetic and biochemical data from previous studies suggest that this mutation can be deleterious (Falck et al. Nature, 410: 842-847, 2001, Bell et al. Science 286: 2528-2531, 1999, Li et al., Mol Cell 9: 1045-1054, 2002). On the other hand, this mutation was found in 2.1% (2/95) of healthy population control individuals in Finland and was proposed as a polymorphism (Vahteristo et al. Cancer Res. 61: 5718-5722, 2001). Other reports also indicate that this mutation is relatively common in normal healthy control individuals (CHEK2 Breast Cancer Consortium, Nature Genet., 31: 55-59, 2002, Allinen et al. Am. J. Hum. Genet., 72: 1023-1028, 2003). This allele does not appear to increase the risk of breast and prostate cancers (Allinen et al., Am. J. Hum. Genet., 72: 1023-1028, 2003). On the other hand one report suggests that I157T variant is a low penetrance allele for prostate cancer (Seppala et al., Br. J. Cancer, 89: 1966-1970, 2003). Whether this functionally related CHEK2 variant confers susceptibility to prostate cancer, or even to other cancers, remained to be clarified.

CDKN2A gene (OMIM 60160) is a tumor suppressor gene regarded as the major melanoma susceptibility gene. (Hashemi et al., Nature, 366: 704-707, 1993). Its protein product p16 is a cyclin-dependent kinase inhibitor that suppresses cell proliferation (Whelan et al., New Eng. J. Med. 33: 975-977, 1995). CDKN2A variants are associated with strong (it is with high penetrance—responsible for strong cancer familial aggregation) predisposition to melanoma and cancers of breast, pancreas and larynx (Whelan et al., New Eng. J. Med., 33: 975-977, 1995; Borg et al., J. Natl. Cancer Inst., 92: 1260-1266, 2000, Smigiel et al., Mol. Carcinog., 39: 147-54, 2004).

In the US Patent Publication US20030175721, CDKN2A variants associated with increased melanoma predisposition have been described. There is also some evidence to indicate a possible association between CDKN2A and head and neck cancer (Schneider-Stock et al., Am. J. Hum. Genet., 72: 216-218, 2003), respiratory malignancies (Belinsky et al., Proc. Natl. Acad. Sci. USA, 95: 11891-11896, 1998) and colorectal cancer (Burri et al., Lab. Invest., 81: 217-229, 2001).

In Poland common CDKN2A variants have been reported. One of them—an alanine to threonine substitution at codon 148 (A148T)—has been estimated to be present in approximately 3-3.5% of the population (Debniak et al., Int. J. Cancer, 110:558-562, 2004; Lamperska et al., Acta Biochim. Pol., 49: 369-376, 2002). Functional studies suggest that this variant is a polymorphism which appears to have no major affect on p16 function (Ranade et al. Nature Genet; 10: 114-

116, 1995; Lilischkis et al. Int. J. Cancer, 66: 249-254, 1996). Nevertheless, the A 148T change has been found to be overrepresented in melanoma kindreds (3%) in comparison To the general population (1.8%) (Queensland, Australia) (Aitken et al., J. Natl. Cancer Inst., 9: 146-452, 1999). Preliminary results of our recent population-based study also suggest that A148T change can be associated with increased melanoma risk. A series of around 400 melanoma cases and around 1000 controls (~500 newborns and ~500 adults) was examined. The Nt442g>a (A148T) prevalence was 2.5-fold increased among melanoma patients. No overrepresentation of the Nt500c>g and the Nt540c>t polymorphisms in Polish melanoma population was observed. The A 148T carrier population (heterozygous G/A alleles) was more likely to have a relative with malignancy compared to the non-carrier population (57% versus 36%, respectively (p=0.03)).

Prostate cancer is a leading cause of morbidity and mortality in men. Outside of the context of a family history, relatively little is known about the genetic determinants that cause prostate cancer. Epidemiological studies suggest that 5-10% of all prostate cancers are attributable to high penetrance susceptibility genes. The strongest evidence for the role of inherited genetic factors in development of prostate cancer comes from a Scandinavian study on twins that suggested that as many as 42%; of prostate cancer risk could be explained by an inherited predisposition (Lichtenstein et al., N. Engl. J. Med., 343: 78-85, 2000). Evidence also points at a complex genetic basis of prostate cancer, involving multiple susceptibility genes and variable phenotypic expression. Different chromosomal loci have been linked to prostate cancer including: HPC1, HPC2, PCAP, CAPB, HPCX, 20q13, 16q23. However, no major prostate susceptibility genes have so far been identified. Only two studies have shown any success cloning candidate susceptibility genes from these regions: HPC1 (MIM 601518) and HPC2/ELAC2 (MIM 605367) (Tavtigian et al., Nature Genet. 27: 172-180, 2001; Carpten et al., Nature Genet., 30: 181-184, 2002). However, other studies suggested a limited role for those genes in hereditary prostate canter (Wang et al., Cancer Res., 61: 6494-6499, 2001.; Xu et al., Am. J. Hum. Genet., 68: 901-911, 2001; and Rebbeck et al., Am. J. Hum. Genet., 67: 1014-1019, 2000).

Breast cancer is a common disease. Each year, approximately 200,000 women in the United States alone are diagnosed with breast cancer, and one in nine American women will develop breast cancer in her lifetime. Hereditary breast cancer is caused by a mutated gene passed from parents to their children. Estimates of the incidence of hereditary breast cancer range from between 5 to 10 percent to as many as 27 percent of all breast cancers.

In 1994, the first gene associated with breast cancer, BRCA1 (BReast CAncer1) was identified on chromosome 17. A year later, a second gene associated with breast cancer, BRCA2, was discovered on chromosome 13. When individuals carry a mutated form of either BRCA1 or BRCA2, they have a high risk of developing breast cancer. Not all hereditary breast cancers are caused by BRCA1 and BRCA2. In fact, a large proportion of breast cancers is not associated with mutation of these two genes.

Despite of longstanding research efforts aimed to develop a mode of diagnosing increased predisposition to cancers of various sites, such diagnostic methods are still needed.

Accordingly, there is a need for the identification of genetic markers that indicate a predisposition for developing cancer and/or malignancies of various sites, (e.g., colorectal cancer, malignant melanoma, such tumors as cancers of the prostate, breast, thyroid, stomach, colon, kidney, lung, pancreas and larynx and myeloproliferative syndrome), that can be used to identify subjects that have an increased susceptibility for developing cancer and/or malignancies, i.e., they are predisposed to develop cancer and/or malignancies.

SUMMARY OF THE INVENTION

We have established that the CHEK2 gene has a role in pathogenesis of prostate, breast, stomach, thyroid, colon or kidney cancers and myeloproliferative syndrome.

Moreover, we have established that the NOD2 gene has a role in pathogenesis of cancers of the breast, colorectum, larynx, lung, ovary, stomach and thyroid gland.

Moreover, we have established that the CDKN2A gene has a role in pathogenesis of malignant melanoma, cancers of breast, colon or lung and also most probably pancreas or larynx.

Specifically, subjects having a mutation in at least one allele of CHEK2 gene and/or at least one allele of NOD2 gene and/or at least one allele of CDKN2A gene have an increased susceptibility for developing specific cancer, i.e., they are predisposed to develop specific cancer. More specifically, we have established that above mentioned genes have roles in low penetrance predisposition to cancers of various sites.

Accordingly, the present invention provides methods and kits for detecting predispositions to cancer in subjects.

The present invention provides a method for detecting a predisposition to cancer in a subject, including detecting in a biological sample from the subject an alteration in the sequence of a gene selected among of CHEK2, NOD2, and CDKN2A genes, wherein:

the alteration in CHEK2 gene is indicative of a predisposition to at least one of the following cancers: prostate, breast, stomach, thyroid, colon or kidney cancers and myeloproliferative syndrome, the alteration in NOD2 gene is indicative of a predisposition to at least one of the following cancers: cancers of the breast, colorectum, larynx, lung, ovary, stomach and thyroid gland, the alteration in CDKN2A gene is indicative of a predisposition to at least one of the following malignancies: malignant melanoma, cancers of breast, colon, lung and also most probably pancreas and larynx.

The present invention further provides a diagnostic kit for identifying a predisposition to at least one of the following cancers: prostate, breast, stomach, thyroid, colon or kidney cancers and myeloproliferative syndrome in a subject, including packaging material and at least two different polynucleotides capable of amplifying at least a region of a CHEK2 gene.

Moreover, the present invention further provides a diagnostic kit for identifying a predisposition to at least one of the following cancers: cancers of the breast, colorectum, larynx, lung, ovary, stomach and thyroid gland in a subject, including packaging material and at least two different polynucleotides capable of amplifying at least a region of a NOD2 gene.

Moreover, the present invention further provides a diagnostic kit for identifying a predisposition to at least one of the following malignancies: malignant melanoma, cancers of breast, colon, lung and also most probably pancreas and larynx in a subject, including packaging material and at least two different polynucleotides capable of amplifying at least a region of a CDKN2A gene.

According to specific aspect of the present invention a detected predisposition is a low penetrance predisposition to cancers of various sites.

BRIEF DESCRIPTION OF THE FIGURES

FIG. 1 depicts a fragment of the genomic sequence of CDKN2A gene, including exon 2 (SEQ ID NO: 1).

FIG. 2 depicts a fragment of the genomic sequence of CARD15/NOD2 gene, including exon 11 (SEQ ID NO: 2).

FIG. 3 depicts a fragment of the genomic sequence of CHEK2 gene, including exon 2, intron 2 and exon 3 (SEQ ID NO: 3).

DETAILED DESCRIPTION OF THE INVENTION

We have established that the CHEK2 gene has a role in pathogenesis of prostate, breast, stomach, thyroid, colon or kidney cancer or myeloproliferative syndrome. Moreover, we have established that the NOD2 gene has a role in pathogenesis of cancers of the breast, colorectum, larynx, lung, ovary, stomach and thyroid gland. Further, we have established that the CDKN2A gene has a role in pathogenesis of malignant melanoma, cancers of breast, colon or lung and also most probably pancreas or larynx.

Accordingly, the present invention provides a method for detecting a predisposition to cancer in a subject, including detecting in a biological sample from the subject an alteration in the sequence of a gene selected among of CHEK2 gene, NOD2 gene, and CDKN2A gene, wherein:

the alteration in CHEK2 gene is indicative of a predisposition to at least one of the following cancers: prostate, breast, stomach, thyroid, colon and kidney cancers or myeloproliferative syndrome, the alteration in NOD2 gene is indicative of a predisposition to at least one of the following cancers: cancers of the breast, colorectum, larynx, lung, ovary, stomach and thyroid gland, the alteration in CDKN2A gene is indicative of a predisposition to at least one of the following malignancies: malignant melanoma, cancers of breast, colon, lung and also most probably pancreas and larynx.

In specific embodiments of the invention a detected predisposition is a low penetrance predisposition to cancers.

The subject may be a human, e.g., of Slavic origin.

In some embodiments of the invention, the alteration in CHEK2 gene is a germline alteration, e.g., IVS2+1G>A or I157T, the alteration in NOD2 gene is a germline alteration, e.g., 3020insC, and the alteration in CDKN2A gene is a germline alteration, e.g. Nt442g>a (A148T). The alteration may be a mutation in one of the mentioned genes, e.g., a mutation caused an insertion into the gene, a deletion of the gene, or a change of nucleotide(s) in the gene. In some embodiments, the alteration in the gene affects, e.g. inhibits, the production of protein encoded by one of the mentioned genes. The alteration may result in the production of a different, e.g. a truncated, protein in comparison to the protein that would be produced by the wildtype one of the mentioned genes. Such a protein may not possess the functional capabilities possessed by the protein encoded by the one of the mentioned genes.

In some embodiments, the alteration can be detected by ASO PGR, SSCP, direct sequencing, ASA-PCR, or RFLP-PCR. The predisposition may be an inherited predisposition. In some embodiments, the biological sample may be a tissue sample such as blood, and the biological sample may include leukocytes.

The present invention further provides a diagnostic kit for identifying a predisposition to at least one of the following cancers: prostate, breast, stomach, thyroid, colon or kidney cancers and myeloproliferative syndrome in a subject, including packaging material and at least two different polynucleotides capable of amplifying at least a region of a CHEK2 gene. In some embodiments of the invention, the amplified region includes IVS2+1G>A mutation or I157T mutation. In some embodiments of the invention, the kit for detection IVS2+1G>A mutation may contain polynucleotides CHEK2ex2/3F and CHEK2ex2/3F. In some embodiments of the invention, the kit for detection I157T mutation may contain polynucleotides Ch157F and Ch157R. The kit may also contain instructions, e.g., instructions for using the kit to identify a predisposition to breast cancer or prostate cancer in a subject.

The present invention further provides a diagnostic kit for identifying a predisposition to at least one of the following cancers: cancers of the breast, colorectum, larynx, lung, ovary, stomach and thyroid gland in a subject, including packaging material and at least two different polynucleotides capable of amplifying at least a region of a NOD2 gene. In some embodiments of the invention, the amplified region includes mutation 3020insC. In some embodiments of the invention, the kit may contain polynucleotides Nod2-wt-nF, Nod2-wt-nR and Nod2-n1-mutR. The kit may also contain instructions, e.g., instructions for using the kit to identify a predisposition to breast cancer or prostate cancer in a subject.

The present invention further provides a diagnostic kit for identifying a predisposition to one of the following malignancies: malignant melanoma, cancers of breast, colon, lung and also most probably pancreas and larynx cancer in a subject, including packaging material and at least two different polynucleotides capable of amplifying at least a region of a CDKN2A gene. In some embodiments of the invention, the amplified region includes mutation Nt442g>a (A148T). In some embodiments of the invention, the kit may contain polynucleotides np16ex2f and np16ex2r. The kit may also contain instructions, e.g., instructions for using the kit to identify a predisposition to breast cancer or prostate cancer in a subject.

The methods and kits provided herein are useful for determining a predisposition for specific cancers such as mentioned above, and they are also useful for diagnosing these cancers at earliest clinical stages.

An alteration in CHEK2 gene, e.g., the IVS2+1G>A alteration or the I157T alteration, an alteration in the NOD2 gene e.g., the 3020insC alteration, or an alteration in the CDKN2A gene, e.g., the A148T alteration, may be detected by any assay available to the art worker that is capable of detecting an alteration, e.g., using nucleotide extension assays, sequencing assays, hybridization assays, amplification assays or immunoassays. An alteration may be detected by performing assays on any form of DNA or RNA or protein obtained from the subject. For example, the art worker could identify an alteration using allele-specific oligonucleotide-PCR (ASO PCR), assays to detect single-stranded conformation polymorphism (SSCP), direct sequencing, allele-specific amplification (ASA), allele-specific hybridization (ASH), and/or restriction fragment length polymorphism analysis after PCR amplification (RFLP-PCR). Hybridization conditions may be performed under various conditions selected by the art worker. Some examples are described hereinbelow.

"Stringent hybridization conditions" and "stringent hybridization wash conditions" in the context of polynucleotide hybridization experiments such as Southern and Northern hybridizations are sequence dependent, and are different under different environmental parameters. Longer sequences hybridize specifically at higher temperatures. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267 (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of polynucleotides is found in Tijssen, Laboratory Techniques in Biochemistry and Molecular Biology Hybridization with Nucleic Acid Probes, part I, chapter 2 "Overview of principles of hybridization and the strategy of polynucleotide probe assays" Elsevier, New York (1993). Generally, highly stringent hybridization and wash conditions are selected to be about 5° C. lower than the thermal melting point ($T_m$) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Molecular Cloning: A Laboratory Manual; Sambrook et al., 3rd Ed., Cold Spring Harbor Laboratory Press, (2001) for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Polynucleotides that do not hybridize to each other under stringent conditions are still substantially identical if the proteins that they encode are substantially identical. This occurs, e.g., when a copy of a polynucleotide is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl. 1% SDS at 37° C., and a wash in 0.5× to 1×SSC at 55 to 60° C.

Several polynucleotides are described here that are useful for detecting the alterations, and the art worker in would be able to design other polynucleotides that would be useful in detecting the alteration. Thus, the present invention also provides polynucleotides comprising, consisting essentially of, or consisting of any of SEQ ID NOs 2-8.

In a still further embodiment the present invention relates to a method of diagnosing a increased inherited predisposition to cancer comprising (a) determining the presence of a polynucleotide including above mentioned mutation in a sample from a subject; and/or (b) determining the presence of a variant form of protein encoded by the mutated variant of gene comprising above mentioned mutation, for example, with the antibody.

Such antibodies specifically recognize a variant of the protein encoded by gene including above mentioned mutation. Antibodies against the variant NOD2, p16 or CHEK2 protein can be prepared by well known methods using a purified protein according to the invention or a (synthetic) fragment derived there from as an antigen. Monoclonal antibodies can be prepared, for example, by the techniques as originally described in Kohler and Milstein, Nature, 256: 7:495, 1975, and Galfr6, Meth. Enzymol. 73:93, 1981, which comprise the fusion of mouse myeloma cells to spleen cells derived from immunized mammals. The antibodies can be monoclonal antibodies, polyclonal antibodies or synthetic antibodies as well as fragments of antibodies, such as Fab. Fv or scFv fragments etc. Furthermore, antibodies or fragments thereof the aforementioned polypeptides can be obtained by using methods which are described, e.g., in Harlow and Lane "Antibodies, A Laboratory Manual", CSH Press, Cold Spring Harbor, 1988.

Human tumors are often associated with genomic instability, and the DNA damage signaling pathway has a crucial role in maintaining of the integrity of genome in response to DNA damaging factors. This pathway may play an important role in pathogenesis of various cancers. Particularly, correlation between changes in CDKN2A gene, CHEK2 gene and NOD2 gene and specific cancers indicated above has not been reported.

A fragment of the genomic sequence of CDKN2A gene (SEQ ED NO: 1), including exon 2, is depicted in FIG. 1. The sequence of exon 2 is shown in bold, and the A148T (nt442G/A) mutation is underlined (also, see Genbank, Accession Number NM_000077; Serrano et al., Nature, 366:704-707, 1993).

A fragment of the genomic sequence of CARD15/NOD2 gene, including exon 11, is depicted in FIG. 2 and as SEQ ID NO:2 The sequence of exon 11 is shown in bold, and the 3020insC is shown in italics. The NOD2 gene (location: 16q12, Genbank, Accession Number AF 178930.1) comprises 12 exons and encodes a protein of 1040 amino acids, the exact function of which remains unknown (Ogura et al., Nature, 411: 603-606, 2001.). The predicted motifs encoded by the NOD2 gene suggest that it is involved in the dysregulation of immune function by either affecting a change in the detection or binding of bacterial proteins and/or impaired nuclear factor-kappaB signaling (Ogura et al., J. Biol. Chem., 276: 4812-4818, 2001.).

A fragment of the genomic sequence of CHEK2 gene, including exon 2, intron 2 and exon 3, is depicted in FIG. 3 and as SEQ ID NO:3. The IVS2+1G>A mutation is shown in italics and underlined. The 430T>C variant (I157T) is shown in bold (also, sec GenBank, Accession Number AF086904.1)

CHEK2 gene (MIM 604373) has 14 exons. It is localised at chromosome 22q and encodes the human analog of yeast Cds1 and Rad53, which are checkpoint kinases. Activation of these proteins in response to DNA damage prevents cellular entry into mitosis. CHEK2 phosphorylates BRCA1 and TP53 proteins, regulating tumor suppressor function of these proteins.

The methods and kits of the invention can be used to determine a subject's predisposition for cancers of various sites, because according to the subject invention the alteration in CHEK2 gene is indicative of a predisposition to at least one of the following cancers: prostate, breast, stomach, thyroid, colon or kidney cancers and myeloproliferative syndrome, the alteration in NOD2 gene is indicative of a predisposition to at least one of the following cancers: breast, colorectum, larynx, lung, ovary, stomach and thyroid gland cancers, and the alteration in CDKN2A gene is indicative of a predisposition to at least one of the following malignancies: malignant melanoma, cancers of breast, colon, lung and also most probably pancreas and larynx.

The invention will now be illustrated by the following non-limiting examples.

EXAMPLE 1

The correlation between a germline alteration in the sequence of the NOD2 gene sequence and inherited predisposition to cancers of various sites, (inter alia cancers of the breast, colorectum, larynx, lung, ovary, stomach and thyroid gland) on example of analysis of 3020insC founder mutation in the NOD2 gene was calculated.

A.) Studies of Correlation Between NOD2 Germline Change 3020insC and Predisposition to Cancers of the Breast, Larynx, Lung, Ovary, Stomach and Thyroid Gland Patients Analyses have been performed in a group of 2604 invasive cancer cases of various sites collected mainly from four large hospitals in the Szczecin area (University Clinic Hospitals, Regional Oncology Hospital and Hospital for Lung Diseases) between 1999 and 2004. Study subjects were asked informed patient consent during outpatient clinic visits to the surgical and medical oncology clinics. In general, patient participation rates exceeded 90% for each cancer site. Patients were consecutive, newly diagnosed cases, unselected for age, sex or family history.

Because of the relatively small number of pancreas cancer patients available to study in the oncology clinics (n=58) the pancreatic cancer sample was supplemented by the inclusion of 69 deceased patients for whom archived material was stored in the Pathology department of the University Clinic Hospital.

The thyroid cancers were all of the papillary type. Cancers were classified according to age of diagnosis (<50 or >50). Because preliminary analyses suggested the excess of invasive breast tumors with an in situ component among cases with the NOD2 mutation, breast cancers were subdivided into subgroups according to the presence or absence of DCIS.

Control group consisted of 910 newborn children from six hospitals throughout Poland (Szczecin, Bialystok, Gorzów Wlkp., Katowice and Wroclaw) in 2003 and of 1000 adults taken at random from patient rolls of three family doctors practicing in the Szczecin region. Material for studies was obtained from peripherial blood lymphocytes for all cases and controls with the exception of 69 pancreatic patients whose DNA was obtained from paraffin—embedded tumor tissue.

Extraction of Genomic DNA 5 ml of peripheral blood was obtained from patients (or umbilical cord of newborns) and mixed with 100 µl 1M EDTA, then was centrifuged in 50 ml polypropylene tubes by 10 minutes at 3000 kg at 4° C. Pellet containing cells was mixed with 45 ml buffer 2× (0.1M $NH_4Cl$, 0.25M $KHCO_3$, 1 mM EDTA) and was left for 15 minutes at 4° C. Supernatant was removed after centrifugation. The remaining pellet with leukocytes was suspended in 2× buffer and centrifugation was repeated three times until pure leukocyte pellet was obtained. Then the leukocytes were mixed with 3 ml digestion buffer (50 mM NaCl, 25 mM $MgCl_2$, 1 mM EDTA, pH 8.0) with 200 µl 10% SDS and 500 µg of Proteinase K. Digestion was carried our 24 h at 37° C.

DNA was purified using phenol/chloroform. In brief digestion products were mixed with 3 ml phenol buffered with 0.5M Tris NCl (pH 8,4), and then 3 ml chloroform and isoamyl alcohol mixture (mixed in proportion 1:25 v/v). Mixture was agitated for about 1 minute and centrifuged 10 minutes at 8000 g and 20° C. After centrifugation, the upper phase was placed to a new tube, mixed with equal volume of chloroform and centrifuged again by 10 minutes at 8000 g. Purification with chloroform was repeated 3-times until protein ring in interphase had disappeared.

The purified water phase containing DNA was mixed with 5M NaCl in proportion 10:1 (v/v) and 96% ethanol in the proportion of water phase with NaCl to ethanol 1:10 (v/v). Mixture was left overnight at 20° C. The resultant DNA pellet was placed in a new tube and purified with 70% ethanol, centrifuged at 3000×g for 5 minutes, and ethanol was poured out. Then, purified DNA pellet was dried in open tube for 30 minutes at 37° C. DNA resuspended in 400 µl TE buffer (25 mM Tris HCl, 1 mM EDTA; pH 18.4) was stored at 4° C. until use.

DNA from paraffin blocks was extracted from five micron sections of formalin-fixed, tissues cut onto slides. From each patient, tissues were sectioned onto six slides. One was hematoxylin/eosin stained. Sections were deparaffinized in two changes of xylene for 5 minutes. Sections were hydrated through a series of graded alcohols (in 96% ethanol (2-times), 70% ethanol and dH2O in each for 5 minutes). Tissues were digested in 1 ml digestion buffer (50 mM Tris HCl, 1 mM CaCl2, pH 8.0) with 20 µl 10% SDS and 500 µg proteinase K. In each series negative controls without tissue were used. Enzymatic digestion was carried out in 55° C. for 2 weeks. At 3rd and 6th day of digestion additional 100 µg proteinase K was added. After digestion, proteinase was heat inactivated at 96° C. for 10 minutes. 500 µl of digestion product was purified in Microcon-100 tubes (Amicon) according to described above procedure. After purification, about 5 µl of solution containing DNA was diluted in 50 µl dH2O.

Allele Specific Amplification (ASA)

The system reported by Ogura Y et al. (Ogura et al., Nature, 411: 603-606, 2001) was giving non-specific results with relatively high frequency in our laboratory. Therefore we have elaborated our own modification of the method without the use of primer specific for normal allele.

ASA reaction was carried out in DNA Thermal Cycler 9600 (Perkin Elmer) in volume of 25 µl containing: 1 µl (50 ng) genomic DNA, 7.5 pmoles of forward primer, 3.75 pmoles of reverse primer, 2 pmoles of mutation specific primer, 2.5 µl PCR buffer (100 mM Tris-HCl, 500 mM KCl, 15 mM $MgCl_2$, 1 mg/ml gelatin; pH 8.6), 0.2 µl solution of dNTP (dATP, dCTP, dGTP, dTTP in concentration 25 µmol/µl of each) and 0.6 U Taq DNA polymerase. For each reaction the positive control (control with DNA from NOD2 heterozygote) and negative controls (control DNA from NOD2 mutation negative patient and control without DNA) were used.

ASA Conditions:
a) Initial denaturation—95° C. 5 minutes
b) 5 cycles, each of:
 denaturation—94° C. 30 s
 primer annealing—59° C. 30 s
 primer elongation—72° C. 30 s
c) 30 cycles, each of:
 denaturation—94° C. 30 s
 primer annealing—58° C. 30 s
 primer elongation—72° C. 30 s Sequence of Primers Used in ASA:

```
Nod2-wt-nF (sense),
5'-CTGAGCCTTTGTTGATGAGC-3'        (SEQ ID NO: 4)

Nod2-wt-nR (antisense),
5'-TCTTCAACCACATCCCCATT-3'        (SEQ ID NO: 5)

Nod2-n1-mutR (antisense and specific to 3020insC),
5'-CGCGTGTCATTCCTTTCATGGGGC-3'    (SEQ ID NO: 6)
```

5 µl of PCR products was mixed with 10 µl loading buffer and electrophoresed in agarose gel (1.5% agarose gel (SeaKem FMC), 1× bufor TBE, 25 µg/ml ethidium bromide) at 8.5 V/cm for 15 minutes. Separated products were visualized in UV light. All cases, in which additional, shorter PCR product was observed, were sequenced in order to confirm the presence of NOD2 gene mutation.

PCR-RFLP

The 3020insC was identified by RFLP-PCR using Apa I (Fermentas). PCR was performed with primers:

```
F 5'-GGCAGAAGCCCTCCTGCAGGGCC-3'   (SEQ ID NO: 7)

R 5'-CCTCAAAATTCTGCCATTCC-3'      (SEQ ID NO: 8)
``` as reported by Helio et al. Gut. 52:558-62 2003, resulting in amplified fragments of 151 bp in size.

PCR reaction was carried out in DNA ThermalCycler 9600 (Perkin Elmer) in volume of 12.5 µl containing: 1 µl (25 ng) genomic DNA, 3.75 pmoles of forward primer, 3.75 pmoles of reverse primer, 1.25 µl PCR buffer (100 mM Tris-HCl, 500 mM KCL, 15 mM $MgCl_2$, 1 mg/ml gelatin; pH 8.6), 0.1 µl solution of dNTP (dATP, dCTP, dGTP, dTTP in concentration 25 µmol/µl of each) and 0.3 U Taq DNA polymerase. For each reaction the positive control (control with DNA from NOD2 heterozygote) and negative controls (control DNA from NOD2 mutation negative patient and control without DNA) were used.

PCR Conditions:
Initial denaturation—95° C. 3 minutes
b) 30 cycles, each of:
 denaturation—94° C. 30 s
 primer annealing—64° C. 30 s
 primer elongation—72° C. 30 s c) final elongation—72° C. 7 minutes Digestion and Electrophoresis Conditions Digestion was performed overnight at 37° C. in volume of 20 µl containing: 12.5 µl PCR product, 6 µl water, 1.6 µl buffer B+ (blue) (Fermentas) and 0.5 U Apa I enzyme. Then, 20 µl of digested product was mixed with 5 µl loading buffer and was electrophoresed in 4% agarose gel with ethidium bromide at 10 V/cm for 20 minutes. Separated PCR products were visualized in UV light. PCR product was digested in cases with the mutation. The following pattern of bands was obtained:

151 bp for control DNA from NOD2 mutation negative patient;

20, 131, and 151 bp for positive control (control with DNA from NOD2 heterozygote);

20, 131 pb for homozygotes (two alleles with 3020insC).

All cases, in which additional, shorter PCR products (131 bp) were observed, were sequenced in order to confirm the presence of the 3020insC mutation.

Sequencing

Exon 11 of the NOD2 gene was amplified with sense and antisense primers in conditions as described in ASA with the only difference—primer specific to 3020insC was not used.

Purification of PCR Products

Products of amplification of exon 11 were put into Microcon-100 sample reservoir (Amicon) dissolved in 400 µl destilled $H_2O$ and centrifuged at 1850×g for 15 minutes. After centrifugation sample reservoir was inserted into a new vial, filled again with 400 µl $H_2O$ and centrifuged at 1850 g for 15 minutes. The latter was repeated three times. Sample reservoir was placed upside down in a new vial and then spinned 3 minutes at 9000 g. All spins were carried out at 25° C. Purified PCR product was diluted in 20 µl destilled $H_2O$.

Sequencing PCR

Asymmetric sequencing PCR was performed in GeneAmp PCR System 9600 thermocycler (Perkin Elmer) in volume of 20 µl containing: 3 pmoles of sense primer, 4 µl purified PCR product, 8 µl BigDye Terminator Ready Reaction Kit v3.0 (Applied Biosystems). In addition, sequencing reaction with antisense primer was carried out to confirm results with the forward primer.

Sequencing Conditions:
Initial denaturation—96° C. 30 s
30 cycles, each of:
 denaturation—94° C. 30 s
 primer annealing—58° C. 30 s
 primer elongation—72° C. 30 s 1 µl 3M sodium citrate (pH 5.0) was added to 20 µl of sequencing product, mixed well and then 60 µl 96% ethanol was added. Probes were centrifuged 20 minutes at 3000×g at 25° C. Then supernatant was removed and 200 µl 70% ethanol was added to purify the pellet. After 5 minute centrifugation at 3000×g at 25° C. supernatant was removed. The pellet was dried in Eppendorf Concentrator 5301 for 20-30 min, and then resuspended in 4 µl of loading buffer (150 µl deionized formamide, 50 µl 50 mM EDTA, 0.05% Dextran Blue). Samples were denaturated for 4 minutes at 94° C., put on ice, and loaded onto denaturating polyacrylamide gel (4% 19:1 polyacrylamide gel, 1× TBE, 6M urea). Electrophoresis was carried out in ABI PRISM 377 DNA Sequencer (Applied Biosystems). Data collection and analysis was performed using ABI PRISM 377 Collection Software and Sequencing Analysis Software Version 3.0 (Applied Biosystems).

Results

The NOD2 3020insC allele was found in 7.3% of individuals in the Polish control population. The prevalence of the NOD2 allele was higher in cancer cases than in controls for eight of the twelve sites studied (Table 1). The excess was statistically significant at the p=0.05level for cancers of the colon, lung and ovary. Odds ratios were generated for all cancers (Table 1) and by age of onset (<50, >50). The association with colon cancer was strong for cancers diagnosed above the age of 50 (OR=2.2; p=0.0006); however the number of patients with colon cancer diagnosed under age 50 was small (n=46). In contrast, the effect of the 3020insC allele was only restricted to laryngeal cancers diagnosed under age 50 (OR=2.9; p=0.009). Similar tendency was observed for consecutive cancers of the stomach and of the thyroid gland) diagnosed under age of 50 (OR 2.1 and 2.0 with p=0.067 and 0.13, respectively). The above results are not statistically significant the most probably due to small size of studied groups (n=56 and 44, respectively). Recent additional studies performed by our group showed that the frequency of 3020insC among patients with familial gastric cancers is obviously increased—20% (10/50). The allele 3020insC did not predispose to breast cancer in the group as a whole, but was seen much more commonly in cases with an intraductal component (18 of 126; 14.3%) than in other subtypes (19 of 336; 5.7%) (p=0.004 for difference). The odds ratio for breast cancer with DOS was 2.1 (p=0.01). The association was particularly strong for breast cancers with DCIS in women diagnosed under age 50 (OR 3.0; p=0.01). For one site (kidney) significantly fewer cases were found to carry the NOD2 allele than expected (OR=0.4; p=0.03).

TABLE 1

Association of NOD2 3020insC mutation and selected types of cancer

| Site | Number tested | Number positive | Prevalence of 3020insC (%) | Odds ratio | p-value |
| --- | --- | --- | --- | --- | --- |
| Bladder | 172 | 18 | 10.5 | 1.5 | 0.13 |
| Breast | 462 | 37 | 8.0 | 1.1 | 0.62 |
| With DCIS | 126 | 18 | 14.3 | 2.1 | 0.009 |
| Without DCIS | 336 | 19 | 5.7 | 0.76 | 0.30 |
| Colon | 255 | 31 | 12.2 | 1.8 | 0.01 |
| Kidney | 245 | 8 | 3.2 | 0.4 | 0.02 |
| Larynx | 223 | 23 | 10.3 | 1.5 | 0.11 |
| Lung | 258 | 30 | 11.6 | 1.7 | 0.03 |
| Melanoma | 198 | 10 | 5.1 | 0.7 | 0.31 |
| Ovary | 317 | 35 | 11.0 | 1.6 | 0.03 |
| Pancreas | 127 | 6 | 4.7 | 0.6 | 0.37 |
| Prostate | 298 | 17 | 5.7 | 0.76 | 0.40 |
| Stomach | 213 | 20 | 9.4 | 1.3 | 0.27 |
| Thyroid | 82 | 8 | 9.8 | 1.4 | 0.39 |
| Controls | 1910 | 140 | 7.3 | | |

B.) Studies of Correlation Between NOD2 Germline Change 3020insC and Predisposition to Colorectal Cancer.

Patients

Five groups of patients have been studied.

Group 1, 250 consecutive CRC patients who underwent surgery in the clinical hospital SPSK-2 Szczecin, Poland; HNPCC patients have been excluded from this group but not patients with undefined cancer familial aggregation where there were at least 2 other malignancies diagnosed on the same side of the family (CFA). All patients in this group are aged older than 50 years.

Group 2, same as group 1 except all 50 patients are under the age of 50 years.

Group 3, 156 patients matching the criteria of HNPCC but without MSH2 or MLH1 constitutional mutations detectable by DNA sequencing.

Group 4, 100 CRC patients from the genetic counseling unit (of the Hereditary Cancer Centre in Szczecin) from families with CFA.

Group 5. Controls—300 consecutive newborns from the clinical hospitals of Szczecin. Genomic DNA isolation, allele specific amplification (ASA) and sequencing were performed as described above.

The frequency of the 3020insC mutation in the consecutive series of colorectal cancer patients over the age of 50 years was, however, significantly elevated compared to the control population. The presence of the 3020insC variant was further investigated and found to be associated with an increased odds ratio of colorectal cancer risk of 2.23, as shown in Table 2. There was no difference between the ages of diagnosis in the group of patients harbouring the 3020insC mutation (average age 65, range 52-78) compared to the patients without the mutation (average age 64, range 51-92).

TABLE 2

Frequency of patients harbouring the 3020insC mutation

| Group | n | % |
| --- | --- | --- |
| Group 1: CRC over 50 years of age | 250 | 14.4 |
| Group 2: CRC under 50 years of age | 50 | 2 |
| Group 3: HNPCC without mutations | 156 | 10.25 |
| Group 4: CFA all ages | 100 | 4 |
| Group 5: Newborns | 300 | 7 |

Chi-squared test

| | OR (CI) | p |
| --- | --- | --- |
| Controls (n = 300) Group 5 vs. | | |
| Group 1 Consecutive CRC over 50 yoa | 2.23 (1.23-4.10) | 0.0046 |
| Group 2 consecutive CRC under 50 yoa. | 0.27 (0.01-1.97) | 0.3010* |
| Group 3 (HNPCC) | 1.48 (0.62-3.44) | 0.3320 |
| Group 4 (CFA) | 0.55 (0.16-1.76) | 0.2840 |
| Group 1 (n = 250) Consecutive CRC over 50 yoa. vs. | | |
| Group 3 | 0.66 (0.29-1.46) | 0.2710 |
| Group 4 | 0.25 (0.07-0.76) | 0.0057 |
| Group 2 (n = 50) Consecutive CRC under 50 yoa vs. | | |
| Group 1 | 8.24 (1.17-165.52) | 0.0149 |
| Group 3 | 5.44 (0.68-116.98) | 0.1500* |
| Group 4 | 2.04 (0.21-49.3) | 0.8720* |
| Group 3 (n = 156) HNPCC vs. | | |
| Group 4 | 0.38 (0.10-1.36) | 0.0967 |

*chi-squared test with Yates correction factor

Further analysis of the study population revealed that there were differences between the lour groups. There was a significant difference in the frequency of the 3020insC mutation between the group of consecutively collected CRC patients under the age of 50 years compared to those over 50 years of age. There was also a significant difference between the colorectal cancer patients who came from families where there was an aggregation of other tumours and the consecutively collected CRC cases diagnosed above 50 years of age. No differences were observed between the all other groups.

Thus we show for the first time that carrier-status of NOD2 3020insC is the marker indicating more than 2.2 increased risk of CRC.

The frequency of the 3020insC mutation in the general population has been estimated in a number of populations to be somewhere in the vicinity of 8% (Hampe et al., Lancet, 357: 1925-1928, 2001) whereas in the population under study here, the frequency has been estimated to be close to 7%. In comparison to the overall frequency reported by Ogura et al (Ogura et al., Nature, 411: 603-606, 2001) there was no significant difference between the Polish population and that from North America (p=0.641).

It could be argued that the control population is unrepresentative to that of the older general population residing in the region in and around the city of Szczecin. Several points suggest that the observed frequency in the newborn population has not significantly changed. First, the frequency of the change corresponds to that or other populations. Second, the population of Szczecin has not experienced a significant influx or outflux of individuals over the past 50 years. Third, the rate of CD has not dramatically increased in recent years. At present, the best examination for prevention and early diagnosis of CRC is coloscopy as well as, developed recently, molecular tests detecting mutations characteristic of cancer in stool. However, their application for entire populations is characterized by low cost effectiveness. Suggested DNA testing is allowing identification of group of patients, for whom coloscopy and molecular analyses of stool should be offered in the first order.

The herein invention, is showing for the first time that constitutional mutation within NOD2 gene (such as 3020insC), is the marker of increased susceptibility to cancers of various sites, especially to tumor types described above. Suggested DNA testing is allowing identification of groups of individuals who should be covered by special programs of surveillance and prevention.

EXAMPLE 2

The correlation between a germline alteration in the sequence of the CHEK2 gene sequence and inherited predisposition to cancers of various sites, inter alia prostate, breast, stomach, thyroid, colon and kidney cancers or myeloproliferative syndrome on example of analysis of IVS2+1G>A, 1100delC and I157T mutations in the CHEK2 gene was calculated.

A) Identification of CHEK2 Variants in the Polish Men with Prostate Cancer.

Patients

The case group for CHEK2 gene sequencing consisted of 96 men with sporadic prostate cancer and 44 men with familial prostate cancer (patients who had one or more first- or second-degree relative with prostate cancer) were diagnosed University Clinic in Szczecin.

Method

Genomic DNA isolation was performed as described above in Example 1.

Template PCR

The entire coding sequence of CHEK2 gene was amplified with pairs of primers and using annealing temperatures as follows (as described previously Dong et al. Am. J. Hum. Genet., 72: 270-80, 2003)

| Exon 1: | 5'-TACTTTTTAATTTTAAGTCTTGTGC-3' (SEQ ID NO: 9) | 58° C. |
|---|---|---|
| | 5'-AAAACGTGATACTATACAACAAAGG-3' (SEQ ID NO: 10) | |
| Exon 2/3: | 5'-ATTTATGAGCAATTTTTAAACG-3' (SEQ ID NO: 11) | 58° C. |
| | 5'-TCCAGTAACCATAAGATAATAATATTAC-3' (SEQ ID NO: 12) | |
| Exon 4: | 5'-ATGAATAAATTTTAGAATCAGTGATCG-3' (SEQ ID NO: 13) | 58° C. |
| | 5'-GAAACCACCAATCACAAATGTATAGTG-3' (SEQ ID NO: 14) | |
| Exon 5: | 5'-GGTAGGTCTCATAATTAAAAACATT-3' (SEQ ID NO: 15) | 58° C. |
| | 5'-TGATCAGCCTTTTATTGGTA-3' (SEQ ID NO: 16) | |
| Exon 6: | 5'-CTCAGGCAGCCTTTTGAGTCAAC-3' (SEQ ID NO: 17) | 58° C. |
| | 5'-CTCTTCTCATATTTTGAGATAGATA-3' (SEQ ID NO: 18) | |
| Exon 7: | 5'-CCTCTTGGGAGTTTCTCACTACTTT-3' (SEQ ID NO: 19) | 53° C. |
| | 5'-CCCCACTACTACATACATACGTT-3' (SEQ ID NO: 20) | |
| Exon 8: | 5'-CTTCTGTCCAAGTGCGT-3' (SEQ ID NO: 21) | 58° C. |
| | 5'-TGCCTAATTCAGGGAGTAAT-3' (SEQ ID NO: 22) | |
| Exon 9: | 5'-TAAGTATCTACTGCATGAATCTGAG-3' (SEQ ID NO: 23) | 58° C. |
| | 5'-CCACATACAGAATGCCAATTTC-3' (SEQ ID NO: 24) | |
| Exon 10*: | 5'-TTA ATT TAA GCA AAA TTA AAT GTC (SEQ ID NO: 25) | 58° C. |
| | 5'-GGC ATG GTG GTG TGC ATC (SEQ ID NO: 26) | |
| Exon 11: | 5'-AGAATGCCACTTGATTTCTTTTC-3' (SEQ ID NO: 27) | 58° C. |
| | 5'-TTTAGCATACCACAAATTCTTAACC-3' (SEQ ID NO: 28) | |
| Exon 12: | 5'-TAATTCTGGCATACTCTTACTGA-3' (SEQ ID NO: 29) | 58° C. |
| | 5'-CCCATGTATTTTATGCTAGCAGG-3' (SEQ ID NO: 30) | |
| Exon 13: | 5'-ATTATCCTTCAGACACAGCTAC-3' (SEQ ID NO: 31) | 58° C. |
| | 5'-TCCTTAAGCCCAGACTACATTT-3' (SEQ ID NO: 32) | |
| Exon 14: | 5'-GTGATTTTCTTTTGAACATTTCTC-3' (SEQ ID NO: 33) | 53° C. |
| | 5'-GTGAAAGAAGGTACATTTC-3' (SEQ ID NO: 34) | |

*-this pair was designed in our department

PCR reactions was carried out in DNA ThermalCycler 9600 (Perkin Elmer) in a volume of 25 µl included: 1 µl (50 ng) genomic DNA, 4 µmol Nbsex6f primer, 6 µmol Nbsex6r primer, 10 µmol Nbsde15 primer, 2.5 µl PCR buffer (100 mM Tris-HCl, 500 mM KCL, 15 mM $MgCl_2$, 1 mg/ml gelatin; pH 8.6), 200 µM each dATP, dCTP, dGTP i dTTP and 1 U Taq DNA polymerase. In each reaction negative control (control without DNA) was used.

PCR Conditions:
c) Initial denaturation—95° C. 5 minutes
b) 35 cycles, each of:
    denaturation—94° C. 30 s
    primer annealing—53-58° C. 45 s
    primer elongation—72° C. 60 s Purification of PCR Products PCR products were pipetted in Microcon-100 sample reservoir (Amicon) placed into vial, 400 µl $dH_2O$ was added to the reservoir and were centrifuged at 1850×g for 15 minutes. After centrifugation sample reservoir was inserted into a new vial, filled with 400 µl $dH_2O$ and centrifuged at 1850×g for 15 minutes. The latter was repeated 3-times. Sample reservoir was placed upside down in a new vial and then spun 3 minutes at 9000×g. All spins were carried out at 25° C. About 5 µl of purified PCR product was seen in the vial and it was diluted in 20 µl $dH_2O$.

Sequencing PCR

Asymmetric sequencing PCR was performed in GeneAmp PCR System 9600 thermocycler (Perkin Elmer) in volume of 20 µl containing: 1 µmol of one of primers from each pair (forward or reverse), 4 µl purified PCR product, 8 µl BigDye Terminator Ready Reaction Kit v3.0 (Applied Biosystems). In addition, in mutation positive cases sequencing reaction was carried to confirm results with the second primer.

Sequencing Conditions:
    Initial denaturation—96° C. 30 s
    30 cycles, each of:
    denaturation—94° C. 30 s
    primer annealing—55° C. 45 s
    primer elongation—72° C. 60 s 20 µl of sequencing product were placed into 0.5 ml Eppendorf tube, 60 µl 96% ethanol and 2 µl 3M sodium citrate (pH 4.6) was added. Probes were centrifuged 20 minutes at 3000 g in 25° C. Then supernatant was removed and 200 µl 70% ethanol was added to purify the pellet. After 5 minute centrifugation in 3000×g at 25° C. supernatant was removed. The pellet was dried in Eppendorf Concentrator 5301 for 20-30 min, and then resuspended in 4 µl of loading buffer (150 µl deionized formamide, 50 µl 50 mM EDTA, 0.05% Dextran Blue). Samples were denaturated for 4 minutes at 94° C., put on ice, and loaded onto a denaturing polyacrylamide gel (4% 19:1 polyacrylamide gel, 1×TBE, 6M urea). Electrophoresis was carried our in ABI PRISM 377 DNA Sequencer (Applied Biosystems). Data collection and analysis was performed using ABI PRISM 377 Collection Software and Sequencing Analysis Software Version 3.0 (Applied Biosystems).

Results

Three CHEK2 variants (IVS2+1G>A, 1100delC and I157T) were detected in 140 men who were fully sequenced.

B) Studies of Correlation Between CHEK2 Germline Changes IVS2+1G>A, I157T and Predisposition to Cancers of Various Sites.

To establish the range of cancer types associated with CHEK2 mutations we genotyped 3915 cases of cancer and 2000 controls in Poland for the three variants detected by sequencing.

These ten cancers include seven of the ten most common types of cancer in Poland, and these represent about two-third of all incident cases in the country. The CHEK2 mutations were analyzed in DNA samples obtained from peripheral blood of adults or from umbilical cord blood of newborns using the method described above. Mutations were confirmed by DNA sequencing. Statistical analysis included the comparison the prevalence of the alleles in cases and controls. For each comparison the entire control series was used for the comparison group. Odds ratios were generated from two-by-two tables and statistical significance was assessed using the Chi-square test.

Because of their different effects on protein synthesis the truncating mutation (IVS2+1G>A) was considered separately from the missense mutation (I157T).

Patients

Cases were collected from four hospitals in the Szczecin area (University Clinic Hospitals, Regional Oncology Hospital and Hospital of Lung Diseases) between 1999 and 2004. Study subjects were asked for their participation at the time of diagnosis or during outpatient visits to the surgical and medical oncology clinics. The series was supplemented with 313 men diagnosed with prostate cancer in the neighbouring cities of Olsztyn, Bialystok, and Opole and with 607 women with breast cancer patients from Koszalin, Poznań, and Opole. In general, patient participation rates exceed 80% for each cancer site. Study subjects were consecutively diagnosed cases, and were unselected for age, sex or for family history. Two control groups were used. The first group consisted of 910 newborn children from five hospitals throughout Poland (Szczecin, Bialystok, Gorzow, Katowice and Wroclaw). The second control group of 1090 unselected adults was taken at random from patient rolls of three family doctors in the Szczecin region. The two control groups were combined to generate estimates for the frequencies of the three alleles in the Polish population in general.

Extraction of Genomic DNA

Extraction of genomic DNA was as described above.

Restriction Fragment Length Polymorphism Polymerase Chain Reaction (RFLP-PCR) RFLP-PCR for the IVS2+1G>A The IVS2+1G>A mutation was identified by RFLP-PCR using Hpy 188III (New England Biolabs). PCR was performed with primers CHEK2ex2/3F:

b 5'-ATTTATGAGCAATTT TTAAAC G-3' (SEQ ID NO: 35) and CHEK2ex2/3R: 5'-TCCAGTAACCATAA-GATAATAATATTA C-3' (SEQ DO NO: 36). PCR conditions were as for template PCR for CHEK2 exon 2/3.

Digestion was performed overnight at 37° C. in volume of 20 µl containing: 5 µl PCR product, 1×NE Buffer 4 (New England Biolabs) and 2U Hpy 188III enzyme. Then, 15 µl of digestion product was mixed with 10 µl loading buffer and was electrophoresed in agarose gel (2% agarose gel (SeaKem FMC), 1× buffer TBE, 25 µg/ml ethidium bromide) at 6V/cm for 30 minutes. Separated PCR products were visualized in UV light. PCR product was digested in cases with the mutation. All cases, in which additional, shorter PCR products were observed, were sequenced in order to confirm the presence of the IVS2+1G>A mutation.

RFLP-PCR for the I157T

The 430T>C variant (Ile157Thr) was analyzed by restriction fragment length polymorphism polymerase chain reaction, using Ch157F (5'-ACCCATGTATCTA (GGAGAGCTG-3' (SEQ ID NO: 37)) and Ch157R (5'-CCACTGTGATCTTCT ATGTCTGCA-3' (SEQ ID NO: 38)) primers. The reverse primer introduced artificial restriction site for PstI enzyme. The PCR products were digested in mutation positive cases. Experimental conditions were as for RFLP-PCR for the IVS2+1G>A with exception of that 2U PstI enzyme (instead of IIpy188III) and NE Buffer 3 (instead of NE Buffer 4) were used and RFLP-PCR products were separated in 3% agarose gel. All cases in which an additional, shorter PCR product was observed, were sequenced in order to confirm the presence of the I157T variant.

Sequencing

The IVS2+1G>A and I157T positive cases detected by RFLP-PCR were confirmed by sequencing using conditions described for sequencing of exons 2/3 of CHEK2 (as described above).

Results

The frequencies of the three CHEK2 variants in cases and controls are presented in Table 3. Because of their different effects on protein synthesis the truncating mutation (IVS2+1G>A) was considered separately from the missense mutation (I157T). A truncating CHEK2IVS2+1G>A mutation was detected in 0.25% of Polish controls. For six of the 13 sites (breast, colon, prostate, thyroid and stomach) the prevalence of the mutant alleles exceeded 1%. For four sites (breast, prostate, thyroid, stomach) the excess was statistically significant ($p<0.01$). The prevalence of this truncating CHEK2 allele was particularly high for patients with thyroid cancer (5%). The missense CHEK2 I157T allele was found in 5.2% of controls. This variant was more common in cancer cases than in controls for five sites, and for three sites (colon, kidney and prostate) and the association was significant ($p<0.01$). In addition, the I157T variant was found in statistical excess in patients with lobular breast cancer (11 positive cases in 100 women with lobular breast cancer, OR 2.2, $p=0.02$). Our study suggests that mutations in CHEK2 appear to increase the risk of cancer in many different organs. Multi-organ cancer predisposition is characteristic of other genes in DNA damage signaling pathway, including BRCA1, BRCA2, and NBS1. We expected that the effects of truncating mutations and of missense mutations might differ. Only prostate cancer was associated with mutations of both types. Breast cancer, thyroid and stomach cancer were associated with the truncating mutation, but not with the missense variant. However, for most sites there were too few cases to distinguish the effects of the two mutations.

TABLE 3

Association between CHEK2 variants and selected types of cancer

| Site | Number tested | Number positive (prevalence), odds ratio, p-value | |
|---|---|---|---|
| | | IVS2 + 1G > A | I157T |
| Bladder | 172 | 1 (0.6%) OR 2.3 p = 0.4 | 12 (7.0%) OR 1.4 p = 0.3 |
| Breast | 1017 | 11 (1.1%) OR 4.4 p = 0.006 | 68 (6.7%) OR 1.3 p = 0.10 |
| Colon | 300 | 1 (0.3%) OR 1.3 p = 0.6 | 28 (9.3%) OR 1.9 p = 0.007 |
| Kidney | 264 | 0 | 26 (9.8%) OR 2.0 p = 0.004 |
| Larynx | 245 | 0 | 10 (4.1%) OR 0.8 p = 0.5 |
| Lung | 272 | 0 | 7 (2.6%) OR 0.5 p = 0.07 |
| Ovary | 292 | 0 | 14 (4.8%) OR 0.9 p = 0.9 |
| Prostate | 690 | 8 (1.2%) OR 4.7. p = 0.007 | 54 (7.8%) OR 1.6 p = 0.01 |
| Stomach | 241 | 4 (1.7%) OR 6.7 p = 0.01 | 13 (5.4%) OR 1.0 p = 0.9 |
| NHL | 120 | 1 OR 3.3 p = 0.3 | 11 (9.2%) OR 1.8 p = 0.09 |
| Pancreas | 93 | 0 | 6 (6.4%) OR 1.3 p = 0.6 |
| Malignant melanoma | 129 | 2 (1.5%) OR 6.3 p = 0.06 | 6 (4.6%) OR 0.9 p = 0.9 |
| Myeloproliferative syndrome | 63 | 0 | 9 (14.3%) OR 3.0 p = 0.0045 |
| Thyroid | 80 | 4 (5%) OR 21 p < 0.0001 | 7 (8.5%) OR = 1.7 p = 0.26 |
| Controls | 2000 | 5 (0.25%) | 104 (5.2%) |

We thus show for the first time that the constitutional mutation IVS2+1G>A and I157T within CHEK2 gene, are markers of increased susceptibility to cancers of various sites, especially to tumor types described above.

Suggested DNA testing is allowing identification of groups of individuals who should be covered by special programmes of surveillance and prevention.

EXAMPLE 3

Verification of the Correlation Between CHEK2 Variants and Predisposition to Cancers of Various Sites on a Larger Series of Cases and Controls than Presented in Example 3

Methods

The methods are described in Example 3.

Patients

To establish the range of cancer types associated with CHEK2 mutations, we genotyped 4008 cases of cancer and 4000 controls in Poland. We included seven of the ten most common types of cancer in Poland, and together these sites represent about two-third of all cancer cases in the country. Cases were collected from hospitals in Szczecin and surrounding counties. Study subjects were asked to participate at the time of diagnosis or during outpatient visits to the surgical and medical oncology clinics. In general, patient participation rates exceed 80% for each cancer site. Study subjects were unselected for age, sex and family history.

Three control groups were combined. The first group consisted of 2000 newborn children from ten hospitals throughout Poland (Szczecin, Bialystok, Gorzow, Katowice, Wroclaw, Poznan, Opole, Lodz and Rzeszow) in 2003 and 2004. Samples of cord blood from unselected infants were forwarded to the study center in Szczecin. The second control group was taken from adult patient rolls of three family doctors practicing in the Szczecin region. 1000 controls were selected at random from the patient lists of these family doctors. The third control group consisted of adults from Szczecin who submitted blood for paternity testing. A sample of DNA was forwarded to the reference laboratory without identifying information. To ensure comparability of the control groups the allele frequencies of the three alleles was computed separately for the adult and neonatal control groups and compared.

Statistical analysis included the comparison of the proportions of the prevalence of the allele in cases and controls. Odds ratios were generated from two-by-two tables and statistical significance was assessed using the Fisher exact test.

Results

The frequencies of the three CHEK2 variants in cases and controls are presented in Table 4.

A truncating CHEK2 mutation was detected in 0.7% of Polish controls. For six of the 13 sites (breast, colon, melanoma, prostate, thyroid and stomach) the prevalence of the mutant alleles exceeded 1%. For three sites (breast, prostate, thyroid) the excess was statistically significant. The prevalence of the truncating CHEK2 alleles was particularly high for patients with thyroid cancer (3.5%). The missense CHEK2 I157T allele was found in 4.8% of controls. This variant was more common in cancer cases than in controls for nine sites, and for five sites (colon, kidney, prostate, thyroid, breast) the association was significant ($p<0.05$).

Although any individual finding might be due to chance, our study on the whole suggests that mutations in CHEK2 increase the risk of cancer in many different organs. There was a total of 52 comparisons made. Of these, 13 were significant at the $p=0.05$ level (2.6 expected by chance) and 5 were significant at the $p=0.01$ level (0.5 expected). Furthermore, for all three sites for which a significant association was seen with the truncating mutation, a significant association was also seen with the missense mutation. This would be unlikely to be the case if the observations were due to chance.

TABLE 4

| | | Number positive (prevalence), odds ratio, p-value | | | |
|---|---|---|---|---|---|
| Site | No. tested | IVS2 + IG > A | 1100delC | Any truncating mutation | I157T |
| Bladder | 172 | 1 (0.6%) OR 1.2 p = 0.7 | 0 | 1 (0.6%) OR 0.8 p = 0.8 | 12 (7.0%) OR 1.5 p = 0.3 |
| Breast | 1017 | 11 (1.1%) OR 2.3 p = 0.04 | 5 (0.5%) OR 2.0 p = 0.3 | 16 (1.6%) OR 2.2 p = 0.02 | 68 (6.7%) OR 1.4 p = 0.02 |
| Colon | 300 | 1 (0.3%) OR 0.7 p = 0.9 | 2 (0.7%) OR 2.7 p = 0.4 | 3 (1%) OR 1.4 p = 0.8 | 28 (9.3%) OR 2.0 p = 0.001 |
| Kidney | 264 | 0 | 2 (0.8%) OR 2.7 p = 0.5 | 2 (0.8%) OR 1.0 p = 0.8 | 26 (9.8%) OR 2.1 p = 0.0006 |
| Larynx | 245 | 0 | 0 | 0 | 10 (4.1%) OR 0.8 p = 0.7 |
| Lung | 272 | 0 | 0 | 0 | 7 (2.6%) OR 0.5 p = 0.1 |
| Melanoma | 129 | 2 (1.5%) OR 3.3 p = 0.3 | 1 (0.8%) OR 3.1 p = 0.8 | 3 (2.3%) OR 3.2 p = 0.1 | 6 (4.6%) OR 1.0 p = 0.9 |
| Ovary | 292 | 0 | 0 | 0 | 14 (4.8%) OR 1.0 p = 0.9 |
| Prostate | 690 | 8 (1.2%) OR 2.5 p = 0.05 | 3 (0.4%) OR 1.7 p = 0.2 | 11 (1.6%) OR 2.2 p = 0.04 | 54 (7.8%) OR 1.7 p = 0.002 |
| Stomach | 241 | 4 (1.7%) OR 3.5 p = 0.047 | 0 | 4 (2.1%) OR 2.3 p = 0.2 | 13 (5.4%) OR 1.1 p = 0.8 |
| NHL | 120 | 1 (0.8%) OR 1.8 p = 0.9 | 0 | 1 (0.8%) OR 1.1 p = 0.7 | 11 (9.2%) OR 2.0 p = 0.05 |
| Pancreas | 93 | 0 | 0 | 0 | 6 (6.4%) OR 1.4 p = 0.6 |
| Thyroid | 173 | 5 (2.9%) OR 6.2 p = 0.0003 | 1 (0.6%) OR 2.3 p = 0.9 | 6 (3.5%) OR 4.9 P = 0.0006 | 15 (8.7%) OR 1.9 p = 0.04 |
| Controls | 4000 | 19 (0.475%) | 10 (0.25%) | 29 (0.725%) | 193 (4.825%) |

EXAMPLE 4

The correlation between a germline alteration in the sequence of the CDKN2A gene sequence and inherited predisposition to cancers of various sites, inter alia malignant melanoma, cancers of the breast, colon, lung and most probably cancers of pancreas and larynx on example of analysis of A148T germline change in the CDKN2A gene was calculated.

Studies of Correlation Between CDKN2A Germline Change and Predisposition to Cancers of Various Sites.

Patients

To establish the range of cancer types associated with A148T change we genotyped 4989 cases of malignancy and 3000 controls in Poland. Cases were collected between 1999-2004, agreed for participation, no selection criteria such as age, sex or cancer family history were used. The control group consisted of 2000 consecutive newborns born in 2003-2004 in nine hospitals throughout Poland (Szczecin, Bialystok, Gorzów, Katowice, Wroclaw, Poznań, Lódź i Rzeszów) and 1000 adults from the region of Szczecin (unselected for the occurrence of malignancies among relatives, male/female ratio 1:1).

Genomic DNA isolation was performed as described above in Example 1.

Restriction Fragment Length Polymorphism Polymerase Chain Reaction (RFLP-PCR)

The A148T mutation was identified by RFLP-PCR using Sac II restriction enzyme (Eurx). PCR was performed with primers:

```
np16cx2f
(5'-AGGGGTAATTAGACACCTGG-3'; SEQ ID NO: 39)
and np16ex2r
(5'-TTTGGAAGCTCTCAGGGTAC-3'; SEQ ID NO: 40).
```

PCR reactions was carried out in DNA ThermalCycler 9600 (Perkin Elmer) in a volume of 25 µl included: 1 µl (50 ng) genomic DNA, 4 µmol np16ex2f primer, 6 µmol np16ex2f primer, 2.5 µl PCR buffer (100 mM Tris-HCl, 500 mM KCL, 15 mM $MgCl_2$, 1 mg/ml gelatin; pH 8.6), 200 µM each dATP, dCTP, dGTP i dTTP and 1 U Taq DNA polymerase. In each reaction negative control (control without DNA) was used.

PCR Conditions:

a) Initial denaturation—95° C. 5 minutes b) 10 cycles, each of:
denaturation—95° C. 30 s
primer annealing—68-58° C. 40 s
primer elongation—73° C. 60 s c) 30 cycles, each of:
denaturation—95° C. 20 s
primer annealing—57° C. 25 s
primer elongation—73° C. 60 s Digestion was performed overnight at 37° C. in volume of 20 µl containing: 5 µl PCR product, 1× NE Buffer 4 (New England Biolabs) and 3U Sac II enzyme. Then, 15 µl of digestion product was mixed with 10 µl loading buffer and was electrophoresed in agarose gel (2% agarose gel (SeaKem FMC), 1× bufor TBE, 25 µg/ml ethidium bromide) at 6V/cm for 30 minutes. Separated PCR products were visualized in UV light. PCR product was digested in cases with the wild type. All cases with alterations detected during electrophoresis were sequenced in order to confirm the presence of the A148T change.

Sequencing PCR

Asymmetric sequencing PCR was performed in GeneAmp PCR System 9600 thermocycler (Perkin Elmer) in volume of 20 µl containing: 1 µmol of one of primers from each pair (forward or reverse), 4 µl purified PCR product, 8 µl BigDye Terminator Ready Reaction Kit v3.0 (Applied Biosystems). In addition, in mutation positive cases sequencing reaction was carried to confirm results with the second primer.

Sequencing Conditions:

Initial denaturation—96° C. 30 s
30 cycles, each of:
denaturation—94° C. 30 s
primer annealing—55° C. 45 s
primer elongation—72° C. 60 s 20 µl of sequencing product were placed into 0.5 ml Eppendorf tubes, and 60 µl 96% ethanol and 2 µl 3M sodium citrate (pH 4.6) was added. Probes were centrifuged 20 minutes at 3000×g in 25° C. Then the supernatant was removed and 200 µl 70% ethanol was added to purify the pellet. After 5 minute centrifugation at 3000×g at 25° C., the supernatant was removed. The pellet was dried in Eppendorf Concentrator 5301 for 20-30 min, and then resuspended in 4 µl of loading buffer (150 µl deionized formamide, 50 µl 50 mM EDTA, 0.05% Dextran Blue). Samples were denaturated for 4 minutes at 94° C., put on ice, and loaded onto denaturating polyacrylamide gel (4% 19:1 polyacrylamide gel, 1×TBE, 6M urea). Electrophoresis was carried our in ABI PRISM 377 DNA Sequencer (Applied Biosystems). Data collection and analysis was performed using ABI PRISM 377 Collection Software and Sequencing Analysis Software Version 3.0 (Applied Biosystems).

Results

The frequency of the A148T variant in cases and controls is presented in Table 5.

TABLE 5

Association between A148T variants and selected types of cancer

|  | A148T | OR | 95% Confidence Interval | p |
|---|---|---|---|---|
| Total controls (n = 3000) | 0 (0%) A/A |  |  |  |
|  | 105 (3.5%) G/A |  |  |  |
|  | 2895 (96.5%) G/G |  |  |  |
|  | Allele A frequency 1.75% |  |  |  |
| Melanoma (n = 411) | 0 (0%) A/A |  |  |  |
|  | 29 (7%) G/A | 2.1 | 1.369-3.201 | 0.0005 |
|  | 382 (93%) G/G | 0.5 | 0.3124-0.7307 | 0.0005 |
|  | Allele A frequency 3.5% | 2.1 | 1.352-3.118 | 0.0006 |
| Bladder (n = 223) | 0 (0%) A/A |  |  |  |
|  | 7 (3.1%) G/A | 0.9 | 0.4105-1.945 | 0.7764 |
|  | 216 (96.9%) G/G | 1.1 | 0.5142-2.436 | 0.7764 |
|  | Allele A frequency 1.6% | 0.9 | 0.4139-1.936 | 0.7784 |
| Breast (n = 1647) | 0 (0%) A/A |  |  |  |
|  | 79 (4.8%) G/A | 1.4 | 1.031-1.872 | 0.0302 |
|  | 1568 (95.2%) G/G | 0.7 | 0.5342-0.9702 | 0.0302 |
|  | Allele A frequency 2.4% | 1.4 | 1.027-1.853 | 0.0319 |

TABLE 5-continued

Association between A148T variants and selected types of cancer

| | A148T | OR | 95% Confidence Interval | p |
|---|---|---|---|---|
| Colon (n = 346) | 0 (0%) A/A | | | |
| | 21 (6.1%) G/A | 1.8 | 1.100-2.886 | 0.0174 |
| | 325 (93.9%) G/G | 0.6 | 0.3465-0.9094 | 0.0174 |
| | Allele A frequency 3% | 1.8 | 1.092-2.827 | 0.0186 |
| Stomach (n = 246) | 0 (0%) A/A | | | |
| | 8 (3.3%) G/A | 0.9 | 0.4461-1.925 | 0.8384 |
| | 238 (96.7%) G/G | 1.1 | 0.5194-2.241 | 0.8384 |
| | Allele A frequency 1.6% | 0.9 | 0.4494-1.916 | 0.8398 |
| Larynx (n = 276) | 0 (0%) A/A | | | |
| | 14 (5.1%) G/A | 1.5 | 0.8216-2.610 | 0.1815 |
| | 262 (94.9%) G/G | 0.7 | 0.3831-1.203 | 0.1815 |
| | Allele A frequency 2.5% | 1.5 | 0.8306-2.570 | 0.1856 |
| Ovary (n = 340) | 0 (0%) A/A | | | |
| | 12 (3.5%) G/A | 1.0 | 0.5491-1.853 | 0.9777 |
| | 328 (96.5%) G/G | 1.0 | 0.5396-1.821 | 0.9777 |
| | Allele A frequency 1.8% | 1.0 | 0.5520-1.843 | 0.9779 |
| Lung (n = 387) | 0 (0%) A/A | | | |
| | 24 (6.2%) G/A | 1.8 | 1.154-2.878 | 0.0090 |
| | 363 (93.8%) G/G | 0.6 | 0.3474-0.8662 | 0.0090 |
| | Allele A frequency 3.1% | 1.8 | 1.146-2.818 | 0.0097 |
| Prostate (n = 348) | 0 (0%) A/A | | | |
| | 13 (3.7%) G/A | 1.1 | 0.5946-1.925 | 0.8215 |
| | 335 (96.3%) G/G | 0.9 | 0.5194-1.682 | 0.8215 |
| | Allele A frequency 1.9% | 1.1 | 0.5972-1.912 | 0.8231 |
| Kidney (n = 264) | 0 (0%) A/A | | | |
| | 6 (2.3%) G/A | 0.6 | 0.2788-1.474 | 0.2915 |
| | 258 (97.7%) G/G | 1.6 | 0.6782-3.586 | 0.2915 |
| | Allele A frequency 1.1% | 0.6 | 0.2820-1.477 | 0.2957 |
| Thyroid (n = 173) | 0 (0%) A/A | | | |
| | 3 (1.7%) G/A | 0.5 | 0.1528-1.549 | 0.2129 |
| | 170 (98.3%) G/G | 2.1 | 0.6454-6.545 | 0.2129 |
| | Allele A frequency 0.9% | 0.5 | 0.1550-1.556 | 0.2169 |
| Non-Hodgkin Lymphoma (n = 162) | 0 (0%) A/A | | | |
| | 6 (3.7%) G/A | 1.1 | 0.4585-2.453 | 0.8909 |
| | 156 (96.3%) G/G | 0.9 | 0.4077-2.181 | 0.9430 |
| | Allele A frequency 1.9% | 1.1 | 0.4796-2.527 | 0.8206 |
| Pancreas (n = 155) | 0 (0%) A/A | | | |
| | 8 (5.1%) G/A | 1.5 | 0.7174-3.138 | 0.2778 |
| | 147 (94.9%) G/G | 0.7 | 0.3186-1.394 | 0.2778 |
| | Allele A frequency 2.5% | 1.5 | 0.7179-3.081 | 0.2822 |

Significantly increased frequency of A148T has been found not only among melanoma patients (Table 4) but also among breast, colorectal and lung cancer cases. The indicated frequency differences point at low penetrance. Overrepresentation of A148T variant was especially high among early-onset melanomas and late-onset colorectal cancers. However small numbers of colorectal cancer diagnosed under 50 yrs (n=63) is the main limitation of this finding.

It cannot be ruled out that CDKN2A alterations (especially A148T) predispose to different malignancies. Although non-significantly but increased incidence of A148T was found also among pancreatic and laryngeal cancer patients. Larger registries of patients are needed in order to evaluate these associations.

Thus we show for the first time that constitutional alteration A148T within CDKN2A gene, is the marker of significantly increased low-penetrant susceptibility to cancers of various sites, especially to tumor types described above. Suggested DNA testing is allowing identification of groups of individuals who should be covered by special programmes of surveillance and prevention.

While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

All publications, patents and patent applications cited herein are herein incorporated by reference.

What is claimed is:

1. A method for detecting in a human subject a predisposition to lung cancer, comprising obtaining a DNA sample from the human subject, and determining whether a 3020insC alteration is present in the NOD2 gene of the human subject, wherein the presence of the 3020insC alteration in the NOD2 gene indicates that said human subject has a predisposition to lung cancer relative to a human subject that does not have the 3020insC alteration.

2. The method of claim 1, wherein the predisposition is a low risk predisposition.

3. The method of claim 1, wherein the 3020insC alteration is a germline alteration.

4. The method of claim 1, wherein the 3020insC alteration is present in the sequence of a single allele of the NOD2 gene.

5. The method of claim 1, wherein the 3020insC alteration is present in the sequence of two alleles of the NOD2 gene.

6. The method of claim 1, wherein the 3020insC alteration is detected by PCR, ligase chain reaction, restriction digestion, direct sequencing, nucleic acid amplification techniques, microchips, hybridization techniques or immunoassays.

7. The method of claim 1, wherein the predisposition is an inherited predisposition.

8. The method of claim 1, wherein the DNA sample is from blood or leukocytes.

9. A method for detecting in a human subject a predisposition to breast cancer, colon cancer, or lung cancer comprising obtaining a DNA sample from the human subject, and determining whether mutation is present in the CDKN2A gene of the human subject that results in a Ala148Thr alteration, wherein the presence of the Ala148Thr alteration indicates that said human subject has a predisposition to breast cancer, colon cancer, or lung cancer relative to a human subject that does not have the Ala148Thr alteration.

10. The method of claim 9, wherein the predisposition to cancer is a predisposition to breast cancer.

11. The method of claim 9, wherein the predisposition to cancer is a predisposition to colon cancer.

12. The method of claim 9, wherein the predisposition to cancer is a predisposition to lung cancer.

13. The method of claim 9, wherein the predisposition is a low risk predisposition.

14. The method of claim 9, wherein the Ala148Thr alteration is a germline alteration.

15. The method of claim 9, wherein the Ala148Thr alteration is present in the sequence of a single allele of the CDKN2A gene.

16. The method of claim 9, wherein the Ala148Thr alteration is present in the sequence of two alleles of the CDKN2A gene.

17. The method of claim 9, wherein the Ala148Thr alteration is detected by PCR, ligase chain reaction, restriction digestion, direct sequencing, nucleic acid amplification techniques, microchips, hybridization techniques or immunoassays.

18. The method of claim 9, wherein the predisposition is an inherited predisposition.

19. The method of claim 9, wherein the DNA sample is from blood or leukocytes.

* * * * *

SEQUENCE LISTING

```
<160> NUMBER OF SEQ ID NOS: 40

<210> SEQ ID NO 1
<211> LENGTH: 1163
<212> TYPE: DNA
<213> ORGANISM: Homo sapiens

<400> SEQUENCE: 1
ctcctccgag cactcgctca cggcgtcccc ttgcctggaa agataccgcg gtccctccag      60
aggatttgag ggacagggtc ggaggggggct cttccgccag caccggagga agaaagagga    120
ggggctggct ggtcaccaga gggtggggcg gaccgcgtgc gctcggcggc tgcggagagg    180
gggagagcag gcagcgggcg gcggggagca gcatggagcc ggcggcgggg agcagcatgg    240
agccttcggc tgactggctg gccacggccg cggcccgggg tcgggtagag gaggtgcggg    300
cgctgctgga ggcggggggcg ctgcccaacg caccgaatag ttacggtcgg aggccgatcc    360
```

```
aggtcatgat gatgggcagc gcccgagtgg cggagctgct gctgctccac ggcgcggagc    420
ccaactgcgc cgaccccgcc actctcaccc gacccgtgca cgacgctgcc cgggagggct    480
tcctggacac gctggtggtg ctgcaccggg ccggggcgcg gctggacgtg cgcgatgcct    540
ggggccgtct gcccgtggac ctggctgagg agctgggcca tcgcgatgtc gcacggtacc    600
tgcgcgcggt gcgggggc accagaggca gtaaccatgc ccgcatagat gccgcggaag      660
gtccctcaga catccccgat tgaaagaacc agagaggctc tgagaaacct cgggaaactt    720
agatcatcag tcaccgaagg tcctacaggg ccacaactgc ccccgccaca acccaccccg    780 cttttcgtagt tttcatttag aaaatagagc ttttaaaaat gtcctgcctt ttaacgtaga   840
tatatgcctt cccccactac cgtaaatgtc catttatatc attttttata tattcttata    900
aaaatgtaaa aagaaaaac accgcttctg cctttcact gtgttggagt tttctggagt      960
gagcactcac gccctaagcg cacattcatg tgggcatttc ttgcgagcct cgcagcctcc    1020
ggaagctgtc gacttcatga caagcatttt gtgaactagg aagctcagg ggggttactg     1080 gcttctcttg agtcacactg ctagcaaatg gcagaaccaa agctcaaata aaaataaaat    1140
aattttcatt cattcactca aaa                                            1163

<210> SEQ ID NO 2
<211> LENGTH: 251
<212> TYPE: DNA
<213> ORGANISM: Homo sapiens

<400> SEQUENCE: 2
tgagcaggat gtgtctaagg gacaggtggg cttcagtaga ctggctaact cctgcagtct    60 cttaactgg acagtttcaa gaggaaaacc aagaatcctt gaagctcacc attgtatctc     120
cttttccagg ttgtccaata actgcatcac ctacctaggg gcagaagccc tcctgcaggc    180
cccttgaaag gaatgacacc atcctggaag tctggtaagg cccctgggca ggcctgtttt    240
agctctccga a                                                         251

<210> SEQ ID NO 3
<211> LENGTH: 402
<212> TYPE: DNA
<213> ORGANISM: Homo sapiens

<400> SEQUENCE: 3
acagaatgtg tgaatgacaa ctactggttt gggagggaca aaagctgtga atattgcttt    60
gatgaaccac tgctgaaaag aacagataaa taccgaacat acagcaagaa cactttcgg    120 attttcaggg taggtaatga atacccatgt atctaggaga gctggtaatt tggtcattgt    180
ttttagatat tttcccacta taaatctctg ctattcaaag tctgaaacaa aatgttctct    240
attttaggaa gtgggtccta aaaactctta cattgcatac atagaagatc acagtggcaa    300
tggaaccttt gtaaatacag agcttgtagg gaaaggaaaa cgccgtcctt tgaataacaa    360
ttctgaaatt gcactgtcac taagcagaaa taaaggtaat at                       402

<210> SEQ ID NO 4
<211> LENGTH: 20
<212> TYPE: DNA
<213> ORGANISM: Homo sapiens

<400> SEQUENCE: 4
ctgagccttt gttgatgagc                                                20
```

```
<210> SEQ ID NO 5
<211> LENGTH: 20
<212> TYPE: DNA
<213> ORGANISM: Homo sapiens

<400> SEQUENCE: 5
tcttcaacca catccccatt                                               20

<210> SEQ ID NO 6
<211> LENGTH: 24
<212> TYPE: DNA
<213> ORGANISM: Homo sapiens

<400> SEQUENCE: 6
cgcgtgtcat tcctttcatg gggc                                          24

<210> SEQ ID NO 7
<211> LENGTH: 23
<212> TYPE: DNA
<213> ORGANISM: Homo sapiens

<400> SEQUENCE: 7
ggcagaagcc ctcctgcagg gcc                                           23

<210> SEQ ID NO 8
<211> LENGTH: 20
<212> TYPE: DNA
<213> ORGANISM: Homo sapiens

<400> SEQUENCE: 8
cctcaaaatt ctgccattcc                                               20

<210> SEQ ID NO 9
<211> LENGTH: 25
<212> TYPE: DNA
<213> ORGANISM: Homo sapiens

<400> SEQUENCE: 9 tacttttaa ttttaagtct tgtgc                                          25

<210> SEQ ID NO 10
<211> LENGTH: 25
<212> TYPE: DNA
<213> ORGANISM: Homo sapiens

<400> SEQUENCE: 10
aaaacgtgat actatacaac aaagg                                         25

<210> SEQ ID NO 11
<211> LENGTH: 22
<212> TYPE: DNA
<213> ORGANISM: Homo sapiens

<400> SEQUENCE: 11
atttatgagc aatttttaaa cg                                            22

<210> SEQ ID NO 12
<211> LENGTH: 28
<212> TYPE: DNA
<213> ORGANISM: Homo sapiens

<400> SEQUENCE: 12
tccagtaacc ataagataat aatattac                                      28
```

<210> SEQ ID NO 13
<211> LENGTH: 27
<212> TYPE: DNA
<213> ORGANISM: Homo sapiens

<400> SEQUENCE: 13
atgaataaat tttagaatca gtgatcg                                         27

<210> SEQ ID NO 14
<211> LENGTH: 27
<212> TYPE: DNA
<213> ORGANISM: Homo sapiens

<400> SEQUENCE: 14
gaaaccacca atcacaaatg tatagtg                                         27

<210> SEQ ID NO 15
<211> LENGTH: 25
<212> TYPE: DNA
<213> ORGANISM: Homo sapiens

<400> SEQUENCE: 15
ggtaggtctc ataattaaaa acatt                                           25

<210> SEQ ID NO 16
<211> LENGTH: 20
<212> TYPE: DNA
<213> ORGANISM: Homo sapiens

<400> SEQUENCE: 16
tgatcagcct tttattggta                                                 20

<210> SEQ ID NO 17
<211> LENGTH: 21
<212> TYPE: DNA
<213> ORGANISM: Homo sapiens

<400> SEQUENCE: 17
ctcaggcagc cttgagtcaa c                                               21

<210> SEQ ID NO 18
<211> LENGTH: 25
<212> TYPE: DNA
<213> ORGANISM: Homo sapiens

<400> SEQUENCE: 18
ctcttctcat attttgagat agata                                           25

<210> SEQ ID NO 19
<211> LENGTH: 25
<212> TYPE: DNA
<213> ORGANISM: Homo sapiens

<400> SEQUENCE: 19
cctcttggga gtttctcact acttt                                           25

<210> SEQ ID NO 20
<211> LENGTH: 23
<212> TYPE: DNA
<213> ORGANISM: Homo sapiens

<400> SEQUENCE: 20
ccccactact acatacatac gtt                                      23

<210> SEQ ID NO 21
<211> LENGTH: 17
<212> TYPE: DNA
<213> ORGANISM: Homo sapiens

<400> SEQUENCE: 21
cttctgtcca agtgcgt                                             17

<210> SEQ ID NO 22
<211> LENGTH: 20
<212> TYPE: DNA
<213> ORGANISM: Homo sapiens

<400> SEQUENCE: 22
tgcctaattc agggagtaat                                          20

<210> SEQ ID NO 23
<211> LENGTH: 25
<212> TYPE: DNA
<213> ORGANISM: Homo sapiens

<400> SEQUENCE: 23
taagtatcta ctgcatgaat ctgag                                    25

<210> SEQ ID NO 24
<211> LENGTH: 22
<212> TYPE: DNA
<213> ORGANISM: Homo sapiens

<400> SEQUENCE: 24
ccacatacag aatgccaatt tc                                       22

<210> SEQ ID NO 25
<211> LENGTH: 24
<212> TYPE: DNA
<213> ORGANISM: Homo sapiens

<400> SEQUENCE: 25
ttaatttaag caaaattaaa tgtc                                     24

<210> SEQ ID NO 26
<211> LENGTH: 18
<212> TYPE: DNA
<213> ORGANISM: Homo sapiens

<400> SEQUENCE: 26
ggcatggtgg tgtgcatc                                            18

<210> SEQ ID NO 27
<211> LENGTH: 23
<212> TYPE: DNA
<213> ORGANISM: Homo sapiens

<400> SEQUENCE: 27
agaatgccac ttgatttctt ttc                                      23

<210> SEQ ID NO 28
<211> LENGTH: 25
<212> TYPE: DNA
<213> ORGANISM: Homo sapiens

<400> SEQUENCE: 28

-continued tttagcatac cacaaattct taacc                                          25

<210> SEQ ID NO 29
<211> LENGTH: 23
<212> TYPE: DNA
<213> ORGANISM: Homo sapiens

<400> SEQUENCE: 29
taattctggc atactcttac tga                                            23

<210> SEQ ID NO 30
<211> LENGTH: 23
<212> TYPE: DNA
<213> ORGANISM: Homo sapiens

<400> SEQUENCE: 30
cccatgtatt ttatgctagc agg                                            23

<210> SEQ ID NO 31
<211> LENGTH: 22
<212> TYPE: DNA
<213> ORGANISM: Homo sapiens

<400> SEQUENCE: 31
attatccttc agacacagct ac                                             22

<210> SEQ ID NO 32
<211> LENGTH: 22
<212> TYPE: DNA
<213> ORGANISM: Homo sapiens

<400> SEQUENCE: 32
tccttaagcc cagactacat tt                                             22

<210> SEQ ID NO 33
<211> LENGTH: 24
<212> TYPE: DNA
<213> ORGANISM: Homo sapiens

<400> SEQUENCE: 33
gtgattttct tttgaacatt tctc                                           24

<210> SEQ ID NO 34
<211> LENGTH: 19
<212> TYPE: DNA
<213> ORGANISM: Homo sapiens

<400> SEQUENCE: 34
gtgaaagaag gtacatttc                                                 19

<210> SEQ ID NO 35
<211> LENGTH: 22
<212> TYPE: DNA
<213> ORGANISM: Homo sapiens

<400> SEQUENCE: 35
atttatgagc aatttttaaa cg                                             22

-continued

```
<210> SEQ ID NO 36
<211> LENGTH: 28
<212> TYPE: DNA
<213> ORGANISM: Homo sapiens

<400> SEQUENCE: 36
tccagtaacc ataagataat aatattac                                          28

<210> SEQ ID NO 37
<211> LENGTH: 22
<212> TYPE: DNA
<213> ORGANISM: Homo sapiens

<400> SEQUENCE: 37
acccatgtat ctaggagagc tg                                                22

<210> SEQ ID NO 38
<211> LENGTH: 24
<212> TYPE: DNA
<213> ORGANISM: Homo sapiens

<400> SEQUENCE: 38
ccactgtgat cttctatgtc tgca                                              24

<210> SEQ ID NO 39
<211> LENGTH: 20
<212> TYPE: DNA
<213> ORGANISM: Homo sapiens

<400> SEQUENCE: 39
aggggtaatt agacacctgg                                                   20

<210> SEQ ID NO 40
<211> LENGTH: 20
<212> TYPE: DNA
<213> ORGANISM: Homo sapiens

<400> SEQUENCE: 40
tttggaagct ctcagggtac                                                   20
```